United States Patent
Virnig et al.

(10) Patent No.: US 6,342,635 B1
(45) Date of Patent: Jan. 29, 2002

(54) KETOXIMES, PROCESSES THEREFOR, AND COPPER EXTRACTION PROCESS

(75) Inventors: Michael J. Virnig, Tucson, AZ (US); Horst Josten, Duesseldorf (DE); Mary Collins, Frankfield (IE); George Wolfe, Tucson; Dustin Gordon, Vail, both of AZ (US); Rainer Eskuchen, Langenfeld; Eugen Heinrichs, Duesseldorf, both of (DE); Frank McDonnell, Cobh; Paul O'Driscoll, Passage West, both of (IE)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/257,532

(22) Filed: Feb. 25, 1999

Related U.S. Application Data

(60) Provisional application No. 60/100,299, filed on Sep. 15, 1998.

(51) Int. Cl.[7] .............................................. C07C 249/08
(52) U.S. Cl. ....................... 564/259; 564/265; 564/266; 568/333; 568/337
(58) Field of Search ................................ 564/259, 265, 564/266; 568/333, 337

(56) References Cited

U.S. PATENT DOCUMENTS

| | | | |
|---|---|---|---|
| 3,224,873 A | 12/1965 | Swanson | 75/101 |
| 3,925,472 A | 12/1975 | Swanson | 260/566 A |
| 4,020,105 A | 4/1977 | Ackerley et al. | 260/566 A |
| 4,020,106 A | 4/1977 | Ackerley et al. | 260/566 A |
| 4,029,704 A * | 6/1977 | Anderson | 260/566 A |
| 4,085,146 A | 4/1978 | Beswick | 260/600 R |
| 4,173,616 A | 11/1979 | Koenders et al. | 423/24 |
| 4,563,256 A | 1/1986 | Sudderth et al. | 204/108 |

\* cited by examiner

Primary Examiner—Peter O'Sullivan
(74) Attorney, Agent, or Firm—John E. Drach; Henry E. Millson, Jr.

(57) ABSTRACT

Ketoximes, processes for their preparation, compositions containing them, and a copper extraction process using the compositions.

One process for the preparation of the ketoximes comprises the following steps:

A) reacting a phenol with a monocarboxylic acid, monocarboxylic acid halide, or monocarboxylic acid anhydride in an inert organic solvent in the presence of an acid catalyst to esterify the phenol;

B) removing any water of reaction produced in step A) either during step A) or in a separate step following step A);

C) adding a Lewis acid to the resulting anhydrous reaction mixture;

D) heating the reaction mixture from step C) to a reaction temperature sufficient to obtain a ketone by the Fries Rearrangement;

E) maintaining the heated reaction mixture for a time period of from 2 to 8 hours at the reaction temperature;

F) at a time of from half to three-quarters of said time period, adding to the heated reaction mixture additional aliphatic monocarboxylic acid, acid halide, or acid anhydride, optionally with additional Lewis acid, and continuing to maintain the heated reaction mixture at the reaction temperature for the remainder of said time period;

G) isolating the ketone reaction product from the reaction mixture; and

H) reacting hydroxylamine or a salt thereof with the ketone obtained in step G) to produce a ketoxime from said ketone.

25 Claims, No Drawings

KETOXIMES, PROCESSES THEREFOR, AND COPPER EXTRACTION PROCESS

CROSS-REFERENCE TO RELATED APPLICATIONS

This application claims priority from U.S. Provisional Application Ser. No. 60/100,299, filed Sep. 15, 1998, the disclosure of which is incorporated herein by reference.

FIELD OF THE INVENTION

This invention relates to processes for the extraction of copper from copper ores, and to compounds useful in such processes.

BACKGROUND OF THE INVENTION

In the extraction of copper from copper ores, various reagents have been used for the extraction, including ketoximes, aldoximes, mixtures of ketoximes and aldoximes, and certain alcohols and esters.

SUMMARY OF THE INVENTION

The present invention relates to an improved process for the preparation of ketoximes, to the ketoximes prepared by the process, to mixtures comprising the ketoximes and aldoximes, and to a process for extracting copper metal from copper ores using the mixtures of ketoximes and aldoximes.

DETAILED DESCRIPTION OF THE INVENTION

Other than in the operating examples, or where otherwise indicated, all numbers expressing quantities of ingredients or reaction conditions used herein are to be understood as modified in all instances by the term "about".

One embodiment of the improved process of the invention for the preparation of ketoximes comprises the following steps:

A) heating at least one phenol ester containing unreacted phenols in an inert organic solvent with a Lewis acid and a monocarboxylic acid halide (preferably chlorine or bromine) or anhydride to obtain a ketone by the Fries Rearrangement;

B) isolating the ketone reaction product from the reaction mixture; and

C) reacting hydroxylamine or a salt thereof with the ketone obtained in step B) to produce a ketoxime from said ketone.

While the above process will work with various phenol esters, it is preferred that in step A) the at least one phenol ester has the formula I or II below:

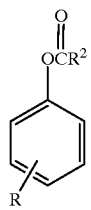
(I)

in which R is an alkyl group having from 1 to 25 carbon atoms, an ethylenically unsaturated aliphatic group containing from 3 to 25 carbon atoms, or —$OR^1$ where $R^1$ is an alkyl group or ethylenically unsaturated aliphatic group as defined above, and $R^2$ is an alkyl group containing 1 to 25 carbon atoms or an ethylenically unsaturated aliphatic group containing 3 to 25 carbon atoms; with the proviso that the total number of carbon atoms in the R and $R^2$ groups is from 3 to 25.

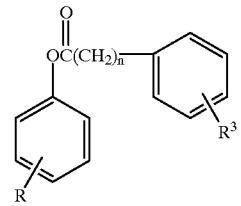

in which R has the same meaning as in formula I; n is 0 or 1; and $R^3$ is an alkyl group having from 1 to 25 carbon atoms, an ethylenically unsaturated aliphatic group containing from 3 to 25 carbon atoms, or —$OR^1$ wherein $R^1$ is an alkyl group or ethylenically unsaturated aliphatic group as defined above, with the proviso that the total number of carbon atoms in the R and $R^3$ groups is from 3 to 25.

The above phenol esters can be readily obtained from the corresponding phenols by methods well known to the art.

The organic solvent is any organic solvent or mixture of solvents which is immiscible with water and inert to the water, to the Lewis acid catalyst, and to the monocarboxylic acid halide or anhydride, e.g. aliphatic and aromatic hydrocarbons, chlorinated hydrocarbons, esters and ethers. Toluene is preferred.

The Lewis acid is preferably aluminum chloride, although other Lewis acids can also be used, such as boron trifluoride. The quantity of Lewis acid can range from 0.9 to 1.5 moles per mole of phenol ester.

While various monocarboxylic acid halides and anhydrides can be used in the present process, the monocarboxylic acid halide or anhydride is preferably selected from compounds of formula III or IV below:

(III)

where $R^2$ is an alkyl group containing 1 to 25 carbon atoms or an ethylenically unsaturated aliphatic group containing 3 to 25 carbon atoms, with the proviso that the total number of carbon atoms in the R group in formula I plus the $R^2$ group in formula III is from 3 to 25; and x is halogen or

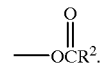

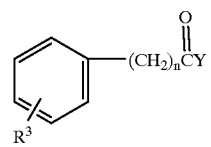
(IV)

where $R^3$ is an alkyl group having from 1 to 25 carbon atoms, an ethylenically unsaturated aliphatic group containing from 3 to 25 carbon atoms, or —$OR^1$ where $R^1$ is an alkyl group or ethylenically unsaturated aliphatic group as defined above; n is 0 or 1; and y is halogen or

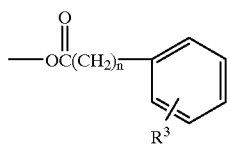

with the proviso that the total number of carbon atoms in the R group in formula II plus the $R^3$ group in formula IV is from 3 to 25.

The $R^2$ or $R^3$ groups in the monocarboxylic acid halide or anhydride can be the same as the $R^2$ or $R^3$ groups in the esters of formulae I and II, or can be different therefrom, but are preferably the same.

The reaction temperature in step A) can range from 50° to 150° C., preferably from 100 to 125° C., and more preferably at the reflux temperature of the mixture.

The mixture is preferably heated for a time period in the range of from 2 to 6 hours.

It is also preferred to add the Lewis acid and monocarboxylic acid halide or anhydride by slow addition during the entire reaction period or during at least a major portion thereof.

It is also preferred to maintain the reaction mixture at the reaction temperature for an additional period (holding period) of from 1 to 4 hours.

For every mole of phenol ester, from 0.5 to 2 moles, preferably from 0.9 to 1.1 moles of Lewis acid is present, and from 0.1 to 1 mole, preferably from 0.2 to 0.6 moles of monocarboxylic acid halide or anhydride is present. The above ranges are however not critical and quantities of components outside these ranges can be employed.

Step B) can be carried out in any convenient manner such as by washing the reaction mixture with water to remove the Lewis acid, and then distilling off the inert organic solvent, followed by distillation to obtain a substantially pure ketone.

Step C) is carried out by heating the mixture to a temperature between 20° and 90° C. until the reaction is substantially complete.

The hydroxylamine or salt thereof is added in approximately molar proportions based on the quantity of ketone reaction product isolated in step B).

Hydroxylamine itself or a salt thereof, such as the sulfate salt, can be used in step C).

The reaction in step C) is preferably carried out in a solvent such as aqueous ethanol or toulene. When a salt of hydroxylamine is used, a base such as sodium carbonate or sodium or potassium hydroxide is added in a quantity sufficient to liberate hydroxylamine.

When the reaction is completed, usually after a few hours, the reaction mixture is neutralized if needed with a mineral acid, and the ketoxime product extracted with a water-immiscible solvent, e.g. chloroform toluene, or kerosene, or if a solid, collected by filtration.

A second embodiment of the improved process of the invention for the preparation of ketoximes comprises the following steps:

A) reacting a phenol with a monocarboxylic acid, acid halide, or acid anhydride in an inert organic solvent in the presence of an acid catalyst to esterify the phenol;

B) removing any water of reaction either during step A or in a separate step following step A);

C) adding a Lewis acid to the resulting anhydrous reaction mixture;

D) reacting the reaction mixture from step C) to a reaction temperature and for a time to convert most of the esterified phenol to a ketone by the Fries Rearrangement;

E) maintaining the reaction for an additional time period of from 2 to 10 hours at the reaction temperature;

F) at a time of from half to three-quarters of said additional time period adding to the heated reaction mixture additional aliphatic monocarboxylic acid, acid halide or acid anhydride, optionally with additional Lewis acid, and continuing to maintain the heated reaction mixture at the reaction temperature for the remainder of said additional time period;

G) isolating the ketone reaction product from the reaction mixture; and

H) reacting hydroxylamine or a salt thereof with the ketone obtained in step G) to produce a ketoxime from said ketone.

In step A) the phenol has the formula:

(V)

where R is an alkyl group having from 1 to 25 carbon atoms, an ethylenically unsaturated aliphatic group containing from 3 to 25 carbon atoms, or an —$OR^1$ group where $R^1$ is an alkyl group or ethylenically unsaturated aliphatic group as defined above.

The monocarboxylic acid, acid halide, or acid anhydride is selected from a compound of formula VI or formula VII below:

(VI)

where $R^2$ is an alkyl group containing 1 to 25 carbon atoms or an ethylenically unsaturated aliphatic group containing 3 to 25 carbon atoms, with the proviso that the total number of carbon atoms in the R group in formula VI plus the $R^3$ group in formula VII is from 3 to 25; and x is —OH, halogen (preferably chlorine or bromine), or

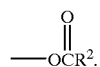

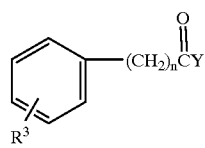

(VII)

is where $R^3$ is an alkyl, group having from 1 to 25 carbon atoms, an ethylenically unsaturated aliphatic group containing from 3 to 25 carbon atoms, or —OR$^1$ where R$^1$ is an alkyl group or ethylenically unsaturated aliphatic group as defined above; n is 0 or 1; and y is OH, halogen (preferably chlorine or bromine), or

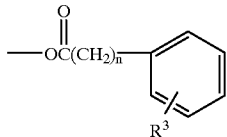

with the proviso that the total number of carbon atoms in the R group in formula V plus the R$^3$ group in formula VII is from 3 to 25.

The organic solvent is any organic solvent or mixture of solvents which is immiscible with water and inert to the water, to the acid catalyst, to the phenol, and to the monocarboxylic acid, acid halide, or acid anhydride, e.g. aliphatic and aromatic hydrocarbons, chlorinated hydrocarbons, esters, and ethers. Toluene is preferred.

The acid catalyst is preferably a sulfonic acid, e.g. methane or p-toluene sulfonic acid. However, other acid catalysts can be used such as a mineral acid, e.g. sulfuric acid, hydrochloric acid, and the like. The catalyst can be present in from 0.1 to 5% by weight, based on the weight of the reactants.

Step A) can be carried out at a temperature of from 30° C. to the boiling point of the organic solvent. Where an organic solvent is used which will azeotrope water, any water of reaction present can be removed as formed. Water of reaction will form when a monocarboxylic acid is used as a reactant.

Preferably, approximately equimolar quantities of reactants are used in step A).

Step B), if needed, can be carried out by heating the reaction mixture until any water present has distilled off.

In step C) the Lewis acid is preferably aluminum chloride, although other Lewis acids can also be used, such as boron trifluoride. The quantity of Lewis acid can range from 0.9 to 1.5 moles per mole of ester formed in step A).

In step D) the reaction temperature can range from 30° C. to 150° C., preferably from 50° C. to 125° C., and more preferably at the reflux temperature of the mixture.

In step F) the additional monocarboxylic acid or derivative thereof and optional Lewis acid is added when the additional time period is from one-half to three-quarters over, e.g. if the additional time period used is 4 hours, then the addition is made during the period of from 2 to 3 hours.

The quantity of additional monocarboxylic acid or derivative thereof can range from 10% to 50% by weight of the quantity present in step A). The quantity of additional Lewis acid, if also added, can range from 1% to 10% of the quantity present in step A).

Steps G) and H) are carried out in the same manner as steps B) and C) in the first embodiment.

A third embodiment of the process of the invention comprises the steps of:

A) reacting a phenol with a monocarboxylic acid halide or anhydride in an inert organic solvent in the presence of a Lewis acid (preferably AlCl$_3$ or BF$_3$) at a temperature and for a time sufficient to esterify the phenol and rearrange the esterified phenol to a ketone;

B) maintaining the heated reaction mixture for an additional time period of from 2 to 10 hours at the reaction temperature;

C) at a time of from half to three-quarters of said additional time period, adding to the heated reaction mixture additional aliphatic monocarboxylic acid or acid halide, optionally with additional Lewis acid, and continuing to maintain the heated reaction mixture at the reaction temperature for the remainder of said additional time period;

D) isolating the ketone reaction product from the reaction mixture; and

E) reacting hydroxylamine or a salt thereof with the ketone obtained in step D) to produce a ketoxime from said ketone.

In the above reaction sequence, the phenol, monocarboxylic acid halide or anhydride and the inert organic solvent are the same as those used in the second process embodiment. Also, steps C) through E) are carried out in the same manner as steps F) through H) of the second embodiment.

The reaction temperature in step A) is from 20° C. to 90° C.

The ketone intermediate products produced by the above process embodiments have the following formulae:

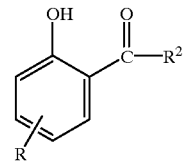

(VIII)

wherein R and R$^2$ have the meaning given above, or

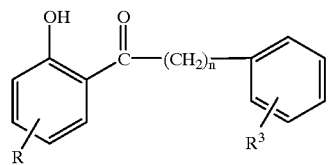

(IX)

wherein R, R$^3$ and n have the meanings given above.

The ketoximes obtained in step C) of the first embodiment, step H) of the second embodiment, and step E) of the third embodiment are the oximes obtained from the above ketones, i.e. ketoximes of the formula:

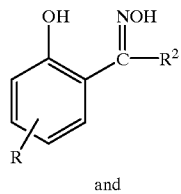

(X)

and

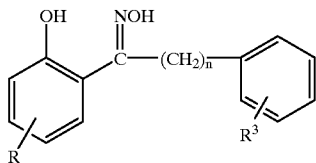

(XI)

The ketones obtained from prior known processes contain a relatively large quantity of unreacted phenols used as starting materials in the preparation of the phenol esters. These unreacted phenols are extremely difficult to separate from the ketone product. Prior processes produce ketones containing 10% by weight or more of unreacted phenols.

The present process results in ketone intermediates containing less than 10%, usually less than 8%, often less than 6%, and even less than 3% by weight of unreacted phenols.

Moreover, the ketoxime products resulting from the oximation of the ketones similarly contain less than 10%, usually less than 8%, often less than 6%, and even less than 3% by weight of unreacted phenols. Hence, the ketoxime products obtained by the processes of the invention have a significantly higher degree of purity than those produced by prior art processes.

In addition, the product yields of ketones and ketoximes are significantly higher than yields obtained by known processes, e.g. a 10% higher yield, since a significant portion of unreacted phenols in the phenol ester starting material is converted to the desired ketone product.

Another advantage lies in the use of the present ketoxime products in the extraction of copper from copper ores, since there is less copper in the raffinate, and hence a higher recovery of copper from the ore.

This invention also relates to reagent compositions useful in the extraction of copper from copper ores, comprising at least one ketoxime of the invention and at least one aldoxime, optionally with one or more of equilibrium modifiers, kinetic active substances, and liquid diluents.

Preferred ketoximes for use in the present compositions are those of formula X above having an isomeric mixture of 7 to 12 carbon alkyl groups as a single substituent on the ring para to the hydroxyl group. Also preferred are compounds wherein the $R^2$ alkyl group is methyl. Consequently, illustrative of preferred phenyl alkyl ketone oxime compounds is 2-hydroxy-5-nonyl phenyl methyl ketone oxime.

Also preferred are benzophenone oxime compounds of Formula Xl having a single alkyl ring substituent having from 7 to 12 carbon atoms in a position para to the hydroxyl group, which alkyl substituent is a mixture of isomers. Examples of such compounds are 2-hydroxyl-5-nonyl benzophenone oxime and 2-hydroxy-5-dodecyl benzophenone oxime which are obtained as mixtures of alkyl isomeric forms when commercial nonylphenol and dodecyl phenol are respectively employed in their synthesis. Preferred phenyl benzyl ketone oximes of Formula (XI) like the above-noted benzophenone oximes, are those having an isomeric mixture of 7 to 12 carbon alkyl groups as a single substituent on the ring para to the hydroxyl group. These preferred compounds are exemplified by the compound, 2-hydroxy-5-nonylphenyl benzyl ketone oxime, as manufactured from a commercial nonylphenol comprising a mixture of nonyl isomeric forms.

The aldoximes useful in the present compositions are those of formula XII below:

(XII)

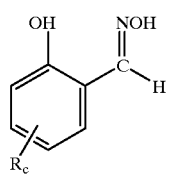

in which R is as defined above with respect to Formulas I and II, c has a value of 1, 2, 3 or 4, and the total number of carbon atoms in $R_c$ is from 3 to 25. Preferred compounds of Formula XII are those wherein c is 1, R is a straight or branched chain alkyl group having from 7 to 12 carbon atoms, and wherein R is attached in a position para to the hydroxyl group. Among these, the more preferred are those wherein R is a mixture of isomers.

Compounds of Formula XII (i.e., hydroxy benzaldoxime compounds, sometimes referred to as "salicylaldoximes") may suitably be prepared according to the methods described in Ackerley, et al., U.S. Pat. No. 4,020,105 or Ackerley, et al., U.S. Pat. No. 4,020,106 or by oximation of aldehydes prepared according to Beswick, U.S. Pat. No. 4,085,146. The above patents are incorporated herein by reference. Again, preferred compounds are those having an isomeric mixture of 7 to 12 carbon alkyl groups as a single substituent para to the hydroxyl group. Mixed alkyl isomeric forms of 2-hydroxy-5-heptyl benzaldoxime, 2-hydroxy-5-octyl benzaldoxime, 2-hydroxy-5-nonyl benzaldoxime and 2-hydroxy-5-dodecyl benzaldoxime are thus preferred.

Compositions of the invention comprise mixtures of one or more ketoximes of Formulas X and XI with one or more aldoximes of Formula XII in molar ratios ranging from 1:100 to 100:1 and preferably from 1:4 to 4:1 with good results being obtained at ratios of 1:1.

Kinetic additive substances may be present in amounts ranging from 0 to 20 mole percent based on ketoxime content and preferably from 0 to 5 mole percent. If present at all, as little as 0.01 mole percent may be used. Preferred kinetic additives include -hydroxy oximes described in Swanson, U.S. Pat. No. 3,224,873 and , β-dioximes described in Koenders, et al., U.S. Pat. No. 4,173,616. The above patents are incorporated herein by reference. A preferred -hydroxy oxime kinetic additive is 5,8-diethyl-7-hydroxydodecan-6-oxime and a preferred dioxime kinetic additive is a mixture of 1-(4'-alkylphenyl)-1,2-propanedione dioximes according to Example 3 of U.S. Pat. No. 4,173,616.

A particularly preferred composition of the invention is a mixture of from 25 to 75 mole % of 2-hydroxy-5-nonylacetophenone oxime prepared by a process of the invention and from 75 to 25 mole % of 5-dodecylsolicylaldoxime.

Equilibrium modifier substances may be incorporated in the formulations of the invention in amounts providing a degree of modification of the hydroxyl aryl aldoxime constituent, in the absence of any hydroxy aryl ketoxime, of from about 0.4 to 1.0 and most preferably from about 0.55 to 1.0. Equilibrium modifiers suitable for use in the present invention include; but are not limited to, long chain (preferably $C_6$–$C_{20}$) aliphatic alcohols such as n-hexanol, n-octanol, 2-ethylhexanol, isodecanol, dodecanol, tridecanol, hexadecanol, and octadecanol; long chain alkylphenols such as heptylphenol, octylphenol, nonlyphenol and dodecylphenol; organophosphorus compounds such as triloweralkyl ($C_4$ to $C_8$) phosphates, especially, tributyl phosphate and tri(2-ethylhexyl)phosphate; and either saturated or unsaturated aliphatic or aromatic-aliphatic esters containing from 10 to 30 carbon atoms. The esters may be polyesters, especially diesters. The esters are preferably highly branched. Optionally the esters may contain other functional groups, more particularly a hydroxyl group.

In the context of this invention 'highly branched' means that the ratio of the number of methyl carbons to non methyl carbons is higher than 1:5.

Especially useful in these compositions and processes are esters derived from certain diacids, preferably branched diacids. Examples include 2,2,4-trimethyl-1,3-pentanediol diisobutyrate and the benzoic acid ester of 2,2,4-trimethyl-1,3-pentanediol monoisobutyrate. The latter esters are commercially available.

The optional diluents include an aliphatic, or aromatic, or mixed aliphatic/aromatic liquid hydrocarbon diluent, especially of the kerosene type commonly employed in solvent extraction processing. Incorporation of a diluent frequently aids the transport and handling of the compositions which may be highly viscous.

The above compositions can be used for extracting copper values from aqueous solutions of copper salts.

The starting material for large scale solvent extraction processing of copper is an aqueous leach solution obtained from a body of ore which contains a mixture of metals in addition to copper. The leaching medium dissolves salts of copper and other metals as it trickles through the ore, to provide an aqueous solution of the mixture of metal values. The metal values are usually leached with sulfuric acid medium, providing an acidic aqueous solution, but can also be leached by ammonia to provide a basic aqueous solution.

The aqueous solution is mixed in tanks with an extraction reagent which is dissolved in an organic solvent, e.g., a kerosene. The reagent includes an extractant chemical which selectively forms metal-extractant complex with the copper ions in preference to ions of other metals. The step of forming the complex is called the extraction or loading stage of the solvent extraction process.

The outlet of the mixer continuously feeds to a large settling tank, where the organic solvent (organic phase), now containing the copper-extractant complex in solution, is separated from the depleted aqueous solution (aqueous phase). This part of the process is called phase separation. Usually, the process of extraction is repeated through two or more mixer/settler stages, in order to more completely extract the desired metal.

After extraction, the depleted aqueous feedstock (raffinate) is either discharged or recirculated to the ore body for further leaching. The loaded organic phase containing the dissolved copper-extractant complex is fed to another set of mixer tanks, where it is mixed with an aqueous strip solution of concentrated sulfuric acid. The highly acid strip solution breaks apart the copper-extractant complex and permits the purified and concentrated copper to pass to the strip aqueous phase. As in the extraction process described above, the mixture is fed to another settler tank for phase separation. This process of breaking the copper-extractant complex is called the stripping stage, and the stripping operation is repeated through two or more mixer-settler stages to more completely strip the copper from the organic phase.

From the stripping settler tank, the regenerated stripped organic phase is recycled to the extraction mixers to begin extraction again, and the strip aqueous phase is customarily fed to an electrowinning tankhouse, where the copper metal values are deposited on plates by a process of electrodeposition. After electrowinning the copper values from the aqueous solution, the solution, known as spent electrolyte, is returned to the stripping mixers to begin stripping again.

In the above process, the extraction reagent is a composition of the invention described above, dissolved in an organic solvent such as a kerosene, i.e. the compositions of the invention can be formulated with an organic solvent, or an organic solvent can be added to the composition prior to use in the above copper extraction process.

The amount of composition used to extract copper from the aqueous leach solution will depend on the concentration of metal salts in the leach solution. For use with aqueous leach solutions containing 1 g. or more per liter of metal, it is preferred to use from 20 to 200 g. of the oximes per liter of organic solution. Suitable relative volumes of organic to aqueous phases can be readily determined. A 1:1 ratio can be used for example.

The invention will be illustrated but not limited by the following examples.

EXAMPLES

Example 1

438 g. nonlyphenol acetate and 428 g. toluene were fed to a 1l. stirred reactor, heated to reflux (115° C.) and dried by decantation of the water from the condensate. Then 220 g. of granulated $AlCl_3$ was charged to the refluxing mixture over a period of 5 hours. At the same time 30 g. of acetyl chloride was continually introduced into the reaction mixture below the surface. When the $AlCl_3$ and acetyl chloride addition was finished, a 3 hour reaction hold time followed at the same reaction temperature. At the end of the reaction hold time the product mixture was transferred to a second reactor filled with 900 g. water at normal temperature and stirred for 15 minutes. The temperature rose to 70–80° C. The stirrer was stopped and after settling the water layer was drained off. A second wash (70–75° C.) was added consisting of 21.38 g. of sodium carbonate dissolved in 833.62 g. of water (i.e. a 2.5% carbonate solution) was added, agitated for 15 minutes, settled for 15 minutes and the aqueous phase drawn off, and finally the product was stripped from the toluene at 20 mbar and 105° C.

450 g. of crude hydroxy nonyl acetophenone was recovered with the following composition:

| Component | Composition (weight %)* |
|---|---|
| Toluene | 0–1 |
| Nonylphenol | 3–6 |
| Nonyl Phenol Acetate | 5–10 |
| Hydroxy Nonyl Acetophenone | 68–74 |
| Alkylated Para Ketones | 2–4 |
| Ortho Hydroxy Acetophenone | 0.5–3 |
| Phenol | 0–0.3 |

*These ranges were obtained from the analysis of the products of several runs.

The product was then fractionated twice under vacuum in a packed column to take out lower and higher boiling impurities. A precut of 10–12% was taken at 6–8 mbar, a bottom temperature of about 175–180° C. and a reflux ratio between 2.5:1 and 5.0:1. In a second step a residue cut of 10 to 15% was taken at 1–3 mbar, 180–200° C. bottom temperature and a reflux ratio of 1.0:1 to 3.0:1.

360 g. of purified hydroxy nonyl acetophenone with the following composition was obtained.

| Component | Composition (weight %)* |
|---|---|
| Nonylphenol | 4–6 |
| Nonyl Phenol Acetate | 5–10 |
| Hydroxy Nonyl Acetophenone | 82–90 |
| Alkylated Para Ketones | 0 |
| Ortho Hydroxy Acetophenone | 0 |
| Phenol | 0 |

*These ranges were obtained from the analysis of the products obtained from several runs.

Comparative Example 1

438 g. of the same nonylphenol acetate used in Ex. 1, and 427 g. toluene were fed to a 1 l. stirred reactor, heated to reflux (115–120° C.) and dried by decantation of the water from the condensate. Then 199.4 g. granulated AlCl$_3$ was charged to the refluxing mixture over a period of 5 hours. The AlCl$_3$ addition was followed by a 1.5 hour reaction hold time at the same reaction temperature. At the end of the reaction hold time the product mixture was transferred to a second reactor filled with 855 g. water at ambient temperature and stirred for 15 minutes. The temperature rose to 70–80° C. The stirrer was stopped and after settling the water layer was drained off. A second wash (70–75 deg. C.) was made consisting of 21.38 g. of sodium carbonate in 833.62 g. of water (i.e. a 2.5% carbonate solution) was added, agitated for 15 minutes, settled for 15 minutes and the aqueous phase drawn off, and finally the product was stripped from the toluene at 20 mbar and 105° C.

407 g. of crude hydroxy nonyl acetophenone was recovered with the following composition:

| Component | Composition (weight %)* |
|---|---|
| Toluene | 0–1 |
| Nonylphenol | 8–12 |
| Nonyl Phenol Acetate | 10–15 |
| Hydroxy Nonyl Acetophenone | 60–65 |
| Alkylated Para Ketones | 2–4 |
| Ortho Hydroxy Acetophenone | 0.5–3 |
| Phenol | 0–1 |

*These ranges were obtained from the anaylsis of the products from several runs.

The product was then fractionated two times under vacuum in a packed column to remove lower and higher boiling impurities. A precut of 12–16% was taken at 6–8 mbar, a bottom temperature of about 175–180° C. and a reflux ratio between 2.5:1 and 5.0:1. In a second step a residue cut of 10 to 15% was taken at 1–3 mbar, 180–200° C. bottom temperature and a reflux ratio of 1.0 to 3.0:1.

315 g. of purified hydroxy nonyl acetophenone with the following composition was obtained.

| Component | Composition (weight %)* |
|---|---|
| Nonylphenol | 10–12 |
| Nonyl Phenol Acetate | 10–15 |
| Hydroxy Nonyl Acetophenone | 78–85 |
| Alkylated Para Ketones | 0 |
| Ortho Hydroxy Acetophenone | 0 |
| Phenol | 0 |

*These ranges were obtained from the anaylsis of the products from several runs.

Example 2

The purified hydroxy nonyl acetophone obtained in Example 1 was oximated to the ketoxime as follows:

360 g. of purified hydroxy nonyl acetophenone, 21.7 g. of water, 10.9 g. of ethyl hexanoic acid, 92.9 g. of sodium carbonate, and 124.7 g. of hydroxylamine sulfate were charged to a 1 l. stirred vessel and heated slowly to 70° C. (+/−5 deg. C.). After a reaction time of 4.5 hours the reaction was complete. After that 206 g. toluene were added for dilution and the product was then washed three times with water at 70° C. The second wash was carried out with a 1% sodium carbonate solution. Finally the toluene was stripped from the reaction mixture at 40 mbar and 110° C. 416 g. of concentrated oxime was obtained. The oxime contained less than 6% by weight of phenols.

Comparative Example 2

The purified hydroxy nonyl acetophenone obtained from the process of Comparative Example 1 was oximated to the ketoxime as follows:

322 g. of purified hydroxy nonyl acetophenone, 20 g. of water, 18.4 g. of water at ambient temperature, 9.2 g. of ethyl hexanoic acid, 78.2 g. of sodium carbonate and 105.7 9. of hydroxylamine sulfate were charged to a 1 l. stirred vessel and heated slowly to 70° C. (+/−5 deg. C.). After a reaction time of 4.5 hours the reaction was complete. After that 175 g. toluene were added for dilution and the product was then washed three times with water at 70° C. The second wash was carried out with a 1 % sodium carbonate solution. Finally the toluene was stripped from the reaction mixture at 40 mbar and 100° C. 353 g. of concentrated oxime was obtained.

The oxime contained about 11 weight % of phenols.

Example 3

Organic solutions were prepared using a commercial 5-nonyl-2-hydroxyacetophenone oxime dissolved in kerosene (LIX® 84-I, Henkel Corporation, Minerals Industry Division, Tucson, Arz.) and the 5-nonyl-2-hydroxyacetophenone oxime obtained in Example 2 also dissolved in kerosene. The concentrations of the above ketoxime solutions were adjusted so that both gave equivalent copper max loads (9.55 gpl and 9.51 gpl respectively).

The concentration of a commercial 5-nonyl salicylaldoxime dissolved in kerosene (LIX® 860 N-I) was adjusted to give a copper max load of 9.55 gpl.

The above ketoxime solutions were then mixed in various ratios with is the aldoxime solution. The organic solutions were then equilibrated with an electrolyte containing 30 gpl of Cu and 185 gpl of sulfuric acid by three separate, 5 minute agitated contacts at an organic/aqueous ratio (O/A)=1. The resultant stripped organics were then equilibrated by shaking for 3 minutes at an O/A=1 with an aqueous copper sulfate solution containing 5.40 gpl of Cu and 1.03 gpl of Fe with a pH of 1.92. The phases were separated and then analyzed for copper content. The results are summarized in Table I below:

TABLE I

| Aldoxime/Ketoxime | LIX ® 84-1 ketoxime | | Example 2 ketoxime | |
|---|---|---|---|---|
| Soln Ratio | Aq. Raff (Cu) | L. Org. (Cu) | Aq. Raff (Cu) | L. Org. (Cu) |
| 100/0 | 1.20 gpl | 8.68 gpl | 1.19 | 8.63 |
| 70/30 | 0.78 gpl | 7.45 gpl | 0.75 | 7.39 |
| 50/50 | 0.75 gpl | 6.52 gpl | 0.73 | 6.52 |
| 30/70 | 0.88 gpl | 5.69 gpl | 0.77 | 5.73 |
| 0/100 | 1.10 gpl | 4.64 gpl | 0.99 | 4.74 |

As can be seen from the above table, the copper content in the aqueous raffinate was significantly lower for the Example 2 ketoxime with the various aldoxime/ketoxime ratios compared to the commercial ketoxime.

Example 4

A laboratory mini-circuit was assembled with 1 parallel stage of extraction and 2 extraction stages in series followed by a single wash stage and one stage of stripping. The aqueous feed solution was a typical heap leach liquor containing 2.63 gpl of Cu and 5.7 gpl of Fe with a pH of 1.63. The lean electrolyte used for stripping consisted of 31.3 gpl Cu, 1.72 gpl Fe, and 216 gpl of sulfuric acid. The aqueous wash solution was prepared by diluting the lean electrolyte down to give an acid concentration of 15 gpl sulfuric acid resulting in a final Cu concentration of 2.23 gpl and 0.12 gpl Fe. Two runs were performed in the same circuit.

The organic phases were prepared in the following manner: A sample of LIX®0860N-I (5-nonylsalicylaldoxime in kerosene diluent) was diluted with additional kerosene to give 3 liters of solution having a copper max load value of 9.8 gpl copper. Also, a sample of LIX®84-I (2-hydroxy-5-nonylacetophenone oxime in kerosene diluent) was diluted with additional kerosene to give 1.5 liters of solution having a copper max load of 8.4 gpl. This was mixed with 1.5 liters of the LIX 860N-I solution to give a final solution having a copper max load value of 9.14 gpl. This is solution 1. A fourth solution was prepared by dissolving 2-hydroxy-5-nonylacetophenone oxime prepared by the process of Example 2 in kerosene to give 1.5 liters of solution having a copper max load of 8.4 gpl. This solution was mixed with the remaining 1.5 liters of LIX 860N-I solution to give solution 2 which had a copper max load of 9.20.

The circuit was operated with O/A flows of 1 in extraction with 2 minute mixer retention times. In the wash stage, the OA flow was 41/1 with a mixer retention time of 2 minutes using aqueous recycle. The strip stage O/A flow was 3.42/1 with a mixer retention time of 2 minutes using aqueous recycle. Each organic was run for a period of several hours. Three to four profiles were collected once the circuit was at equilibrium. The results from the profiles were averaged to give a value for each data point. The metallurgical performance data is summarized in the following Table.

TABLE 2

| Organic | % Cu Recovery | % Cu Max Load | Cu/Fe Pre-Wash | Cu/Fe Post Wash |
|---|---|---|---|---|
| 1 | 84.2 | 79.1 | 292 | 782 |
| 2 | 84.4 | 78.9 | 335 | 1022 |

As can be seen from the data, the use of the 2-hydroxy-5-nonlyacetophenone oxime from the process of this invention results in significantly less transfer of iron to the tankhouse than does material produced by the present commercial process. To maintain the iron level in the tankhouse electrolyte in an acceptable range, operators have to bleed a certain percentage of the electrolyte out of the tankhouse. This results in significant costs due to losses of sulfuric acid and cobalt. Reducing the iron transferred to the tankhouse reduces the amount of bleed required to maintain the iron level.

What is claimed is:

1. A process for the preparation of ketoximes comprising the steps of:
   A) heating at least one phenol ester containing an unreacted phenol in an inert liquid organic solvent with a Lewis acid and a monocarboxylic acid halide or anhydride to obtain a ketone by the Fries Rearrangement;
   B) isolating the ketone reaction product from the reaction mixture; and
   C) reacting hydroxylamine or a salt thereof with the ketone obtained in step B) to produce a ketoxime from said ketone.

2. The process of claim 1 wherein in step A) the at least one phenol ester is selected from the group consisting of compounds of the formula I and II below:

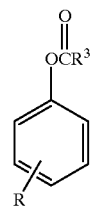

in which R is an alkyl group having from 1 to 25 carbon atoms, an ethylenically unsaturated aliphatic group containing from 3 to 25 carbon atoms, or —$OR^1$ wherein $R^1$ is an alkyl group or ethylenically unsaturated aliphatic group as defined above; and $R^2$ is an alkyl group containing 1 to 25 carbon atoms or an ethylenically unsaturated aliphatic group containing 3 to 25 carbon atoms, with the proviso that the total number of carbon atoms in the R and $R^2$ groups is from 3 to 25; and

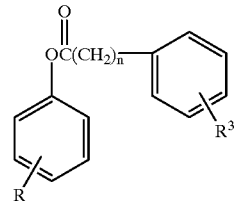

in which R has the same meaning as in formula I; n is 0 or 1; and $R^3$ is an alkyl group having from 1 to 25 carbon atoms, an ethylenically unsaturated aliphatic group containing from 3 to 25 carbon atoms, or —$OR^1$ where $R^1$ is an alkyl group or ethylenically unsaturated aliphatic group as defined above; with the proviso that the total number of carbon atoms in the R and $R^3$ groups is from 3 to 25.

3. The process of claim 2 wherein the Lewis acid is $AlCl_3$.

4. The process of claim 2 wherein the inert organic solvent is selected from the group consisting of aliphatic hydrocarbons, aromatic hydrocarbons, chlorinated hydrocarbons, esters, and ethers.

5. The process of claim 2 wherein the monocarboxylic acid halide or anhydride is selected from the group consisting of:

a) compounds of the formula:

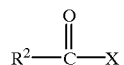

where $R^2$ is an alkyl group containing 1 to 25 carbon atom or an ethylenically unsaturated aliphatic group containing 3 to 25 carbon atoms, with the proviso that the total number of carbon atoms in the R group in formula I plus the $R^2$ group in formula II is from 3 to 25; and X is halogen or

b) compounds of the formula:

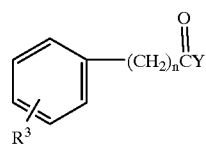
(IV)

where $R^3$ is an alkyl group having from 1 to 25 carbon atoms, an ethylenically unsaturated aliphatic group containing from 3 to 25 carbon atoms, or —$OR^1$ where $R^1$ is an alkyl group or ethylenically unsaturated aliphatic group as defined above; n is 0 or 1, and Y is halogen or

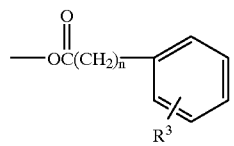

with the proviso that the total number of carbon atoms in the R group in formula I and the $R^3$ group in formula IV is from 3 to 25.

6. The process of claim 2 wherein the reaction temperature in step A) is in the range of from about 50 to 150° C.

7. The process of claim 6 wherein the reaction temperature is the reflux temperature of the mixture.

8. The process of claim 2 wherein the Lewis acid and monocarboxylic acid or anhydride are added by slow addition over a period of from about 2 to about 6 hours.

9. The process of claim 8 wherein the reaction mixture is kept at the reaction temperature for an additional period of from about 1 to about 4 hours.

10. The process of claim 2 wherein step C) is carried out at a temperature in the range of from about 20° to about 90° C.

11. A process for the preparation of ketoximes comprising the steps of:
A) reacting a phenol with a monocarboxylic acid, monocarboxylic acid halide, or monocarboxylic acid anhydride in an inert organic solvent in the presence of an acid catalyst to esterify the phenol;
B) removing any water of reaction produced in step A) either during step A) or in a separate step following step A);
C) adding a Lewis acid to the resulting anhydrous reaction mixture;
D) reacting the reaction mixture from step C) to a reaction temperature and for a tire to convert most of the esterified phenol to a ketone by the Fries Rearrangement;
E) maintaining the reaction for an additional time period of from 2 to 10 hours at the reaction temperature;
F) at a time of from half to three-quarters of said additional time period adding to the heated reaction mixture additional aliphatic monocarboxylic acid, acid halide, or acid anhydride, optionally with additional Lewis acid, and continuing to maintain the heated reaction mixture at the reaction temperature for the remainder of said additional time period;
G) isolating the ketone reaction product from the reaction mixture; and
H) reacting hydroxylamine or a salt thereof with the ketone obtained in step G) to produce a ketoxime from said ketone.

12. The process of claim 11 wherein in step A) the phenol has the formula:

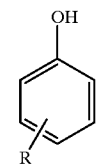
(V)

where R is an alkyl group containing from 1 to 25 carbon atoms, an ethylenically unsaturated aliphatic group containing from 3 to 25 carbon atoms, or —$OR^1$ where $R^1$ is an alkyl group or ethylenically unsaturated aliphatic group as defined above; and the monocarboxylic acid, acid halide, or acid anhydride is selected from the group consisting of:

a) a compound of formula VI:

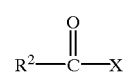
(VI)

where $R^2$ is an alkyl group containing 1 to 25 carbon atoms or an ethylenically unsaturated aliphatic group containing 3 to 25 carbon atoms, with the proviso that the total number of carbon atoms in the R group in formula V plus the $R^2$ group in formula VI is from 3 to 25 and X is —OH, halogen, or

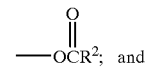

b) a compound of formula VII:

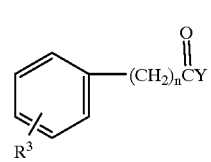
(VII)

where $R^3$ is an alkyl group having from 1 to 25 carbon atoms, an ethylenically unsaturated aliphatic group containing from 3 to 25 carbon atoms, or an —$OR^1$ where $R^1$ is an alkyl group or ethylenically unsaturated aliphatic group as defined above; n is 0 or 1, and Y is —OH, halogen, or

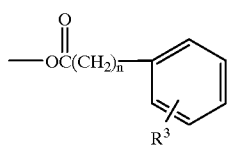

with the proviso that the total number of carbon atoms in the R group in formula V plus the $R^3$ group in formula VII is from 3 to 25.

13. The process of claim 11 wherein in step A) the inert organic solvent is an organic solvent or mixture of solvents which is immiscible with water and inert to the water, the acid catalyst, the phenol, and the monocarboxylic acid, acid halide, or acid anhydride.

14. The process of claim 13 wherein the inert organic solvent is toluene.

15. The process of claim 11 wherein in step A) the acid catalyst is a sulfonic acid.

16. The process of claim 11 wherein in step A) the reaction temperature is in the range of from about 30° C. to the boiling point of the inert organic solvent.

17. The process of claim 11 wherein in step C) the Lewis acid is aluminum chloride.

18. The process of claim 11 wherein in step D) the reaction temperature is in the range of from about 30° to about 150° C.

19. The process of claim 18 wherein the reaction temperature is the reflux temperature of the mixture.

20. The process of claim 11 wherein in step F) both additional aliphatic monocarboxylic acid, acid halide, or acid anhydride, and Lewis acid are added to the heated reaction mixture.

21. The process of claim 20 wherein the quantity of additional monocarboxylic acid, acid halide, or acid anhydride is from about 10% to about 50% by weight of the quantity present in step A), and the quantity of Lewis acid is from about 1% to about 10% of the quantity present in step A).

22. The process of claim 11 wherein in step G) the reaction mixture from step F) is washed with water, and the inert organic solvent is distilled off.

23. The process of claim 11 wherein step H) is carried out at a temperature of from 20° to 90° C.

24. A process for the preparation of ketoximes comprising the steps of:
A) reacting a phenol with a monocarboxylic acid halide or anhydride in an inert organic solvent in the presence of a Lewis acid at a temperature and for a time sufficient to esterify the phenol and rearrange the esterified phenol to a ketone;
B) maintaining the heated reaction mixture for an additional time period of from 2 to 10 hours at the reaction temperature;
C) at a time of from half to three-quarters of said additional time period, adding to the heated reaction mixtures additional aliphatic monocarboxylic acid or acid halide, optionally with additional $AlCl_3$ or $BF_3$, and continuing to maintain the heated reaction mixture at the reaction temperature for the remainder of said additional time period;
D) isolating the ketone reaction product from the reaction mixture; and
E) reacting hydroxylamine or a salt thereof with the ketone obtained in step D) to produce a ketoxime from said ketone.

25. The process of claim 24 wherein in step A) the phenol has the formula:

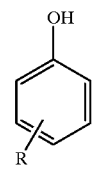

(V)

where R is an alkyl group having from 1 to 25 carbon atoms, an ethylenically unsaturated aliphatic group containing from 3 to 25 carbon atoms, or $—OR^1$ where $R^1$ is an alkyl group or ethylenically unsaturated aliphatic group as defined above; and the monocarboxylic acid, acid halide, or acid anhydride is selected from the group consisting of:
a) a compound of formula VI:

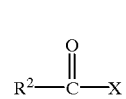

(VI)

where $R^2$ is an alkyl group containing 1 to 25 carbon atoms or an ethylenically unsaturated aliphatic group containing 3 to 25 carbon atoms, with the proviso that the total number of carbon atoms in the R group in formula V plus the $R^2$ group in formula VI is from 3 to 25; and X is —OH, halogens, or

; and b) a compound of formula VII:

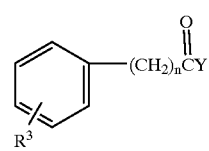

(VII)

where $R^3$ is an alkyl group having from 1 to 25 carbon atoms, an ethylenically unsaturated aliphatic group containing from 3 to 25 carbon atoms, or $—OR^1$ where $R^1$ is an alkyl group or ethylenically unsaturated aliphatic group as defined above; n is 0 or 1; and Y is —OH halogen, or

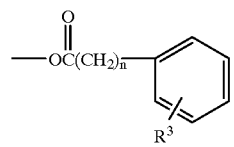

with the proviso that the total number of carbon atoms in the group of formula V plus the $R^3$ group of formula VII is from 3 to 25.

* * * * *